United States Patent [19]

Barriere

[11] Patent Number: 4,791,293
[45] Date of Patent: Dec. 13, 1988

[54] APPARATUS FOR THE REMOTE EXAMINATION OF FAULTS EMERGING ON THE INNER SURFACE OF A DEEP CAVITY

[75] Inventor: André Barriere, Morsang sur Orge, France

[73] Assignee: Commissariat a l'Energie Atomique, Paris, France

[21] Appl. No.: 915,745

[22] Filed: Oct. 6, 1986

[30] Foreign Application Priority Data

Oct. 7, 1985 [FR] France .................... 85 14819

[51] Int. Cl.⁴ .......................................... G01N 21/88
[52] U.S. Cl. .................... 250/302; 250/458.1; 350/96.2
[58] Field of Search ............... 250/302, 303, 492.1, 250/461.1, 458.1, 372; 350/96.2, 96.26

[56] References Cited

U.S. PATENT DOCUMENTS

| 3,409,897 | 11/1968 | Bosselaar et al. | 346/33 |
| 3,761,186 | 9/1973 | Wason | 356/241 |
| 4,398,791 | 8/1983 | Dorsey | 350/96.2 |
| 4,548,466 | 10/1985 | Evans et al. | 350/96.2 |
| 4,562,348 | 12/1985 | Brogardh et al. | 250/231 P |
| 4,577,109 | 3/1986 | Hirschfeld | 250/461.1 |
| 4,582,809 | 4/1986 | Block et al. | 250/227 |

FOREIGN PATENT DOCUMENTS 0083759 7/1983 European Pat. Off. .
777621 11/1980 U.S.S.R. .................... 350/96.26
1207090 9/1970 United Kingdom .
2105048 8/1981 United Kingdom .

OTHER PUBLICATIONS

Manufacturing Technology Note, report No. WVT--QA-7801, Oct. 1979, NTIS, Springfield, U.S.; "Laser Scan for Bore Inspection".
Review of Scientific Instruments, vol. 51, No. 10, Oct. 1980, pp. 1403-1406, American Institute of Physics, New York, U.S.; J. H. Kinsey et al.: "Endoscopic System for Simultaneous Visual Examination and Electronic Detection of Fluorescence".

Primary Examiner—Carolyn E. Fields
Assistant Examiner—John A. Miller

[57] ABSTRACT

It comprises a monochromatic radiation source; an optical fibre connected by one end to the radiation source and by the other end to an observation probe for transmitting the monochromatic radiation from the source to the observation probe and the photoluminescent radiation from the probe to signal processing means; an observation probe able to move in the cavity and having a mirror inclined with respect to the surface to be observed for directing the radiation transmitted by the optical fibre towards said wall and for reflecting a return radiation to a return optical fibre conducting it to processing means; and a rotary optical connection placed on the optical fibre for permitting the continuity of the optical line and the advance of the probe without any corkscrewing of said optical fibre.

9 Claims, 4 Drawing Sheets

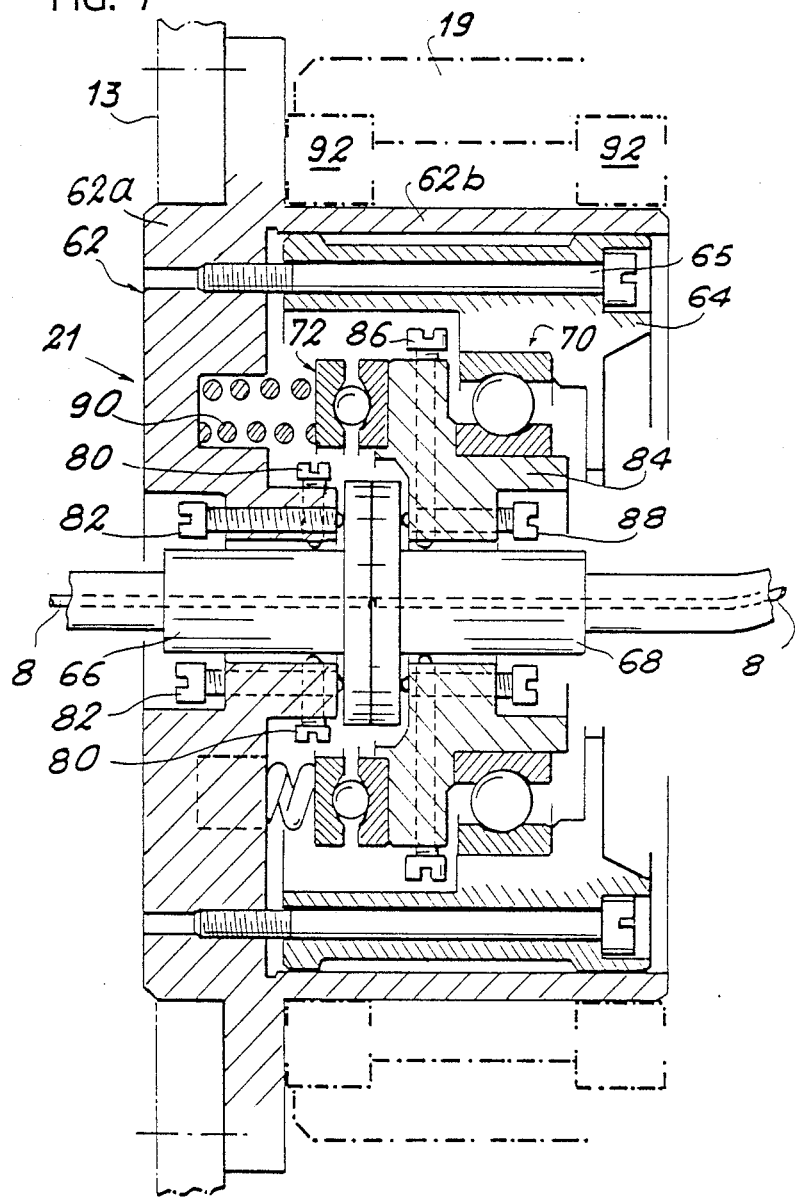

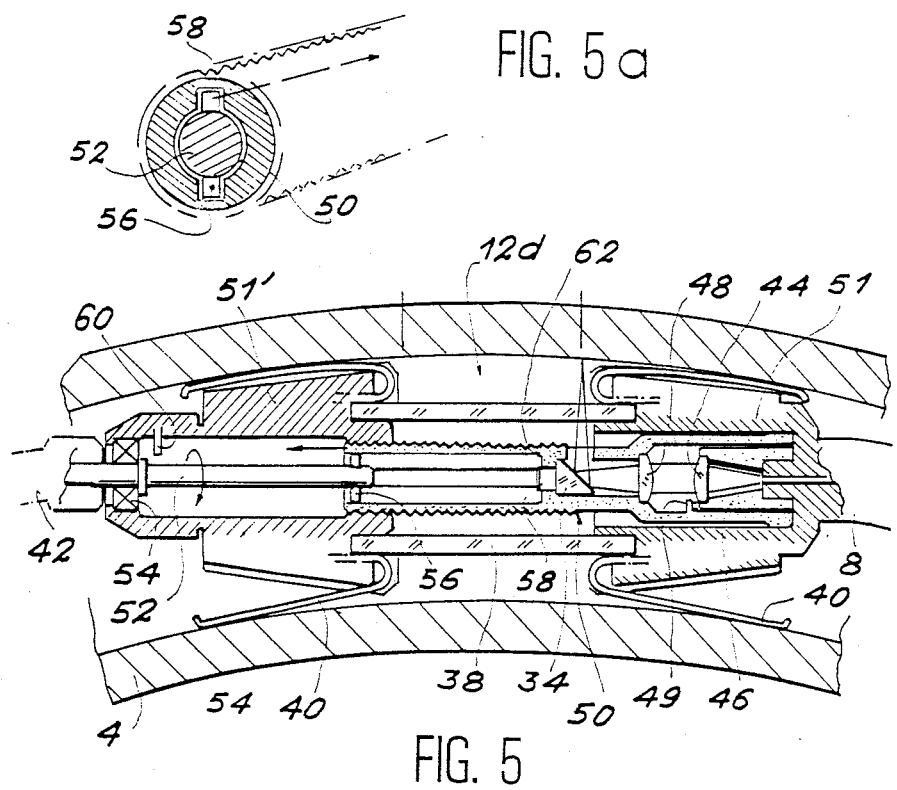
FIG. 5a
FIG. 5
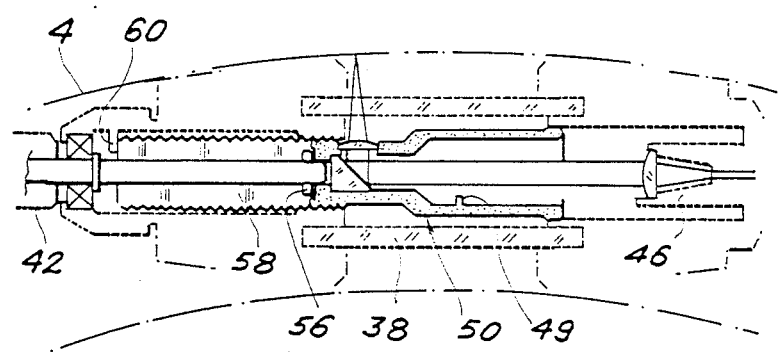
FIG. 6

APPARATUS FOR THE REMOTE EXAMINATION OF FAULTS EMERGING ON THE INNER SURFACE OF A DEEP CAVITY

BACKGROUND OF THE INVENTION

The present invention relates to an apparatus for the remote examination of faults or defects emerging on the inner surface of a deep cavity. More specifically, said apparatus utilizes the photoluminescence of a so-called penetrating substance, which is selectively fixed in or on the surface defects of the deep cavity.

Among the presently most widely used methods for investigating surface faults or defects on mechanical parts and particularly on tubes, reference can more particularly be made to gammagraphy, neutronography, ultrasonics, eddy currents and dye penetrant inspection.

The latter method is widely used for investigating faults emerging on the surface and whose small size does not make it possible to observe them with the naked eye. The principle of dye penetrant inspection is as follows. The area to be observed is impregnated with a liquid having a high penetrating power and which contains tracers becoming fluorescent when they are excited by an ultraviolet light.

The defects emerging on the surface and no matter what their size, are filled with this liquid and form microreservoirs. This liquid or penetrant is then eliminated from the surface by rinsing e.g. with water.

Certain of these liquids, called auto-penetrants, as a result of interfacial tension and adsorption phenomena, reappear on the surface after a certain time, thereby revealing microdefects within which they had infiltrated by the emission of an intense, bright light when illuminated by ultraviolet light.

The first apparatuses using ultraviolet radiation for investigating faults and defects had mercury vapour or black light lamps, whose dimensions were to large to permit their introduction into small cavities, such as small diameter tubes. An attempt was made to use miniaturized lamps incorporated into the end of endoscopes. However, such apparatuses suffered from the disadvantages that they had a low illuminating power and gave off a large amount of heat.

An attempt was also made to use light guides, either in the form of glass fibres, or in the form of liquids. However, for wavelengths between 380 and 400 nanometers, these different guides do not make it possible to exceed a luminous flux of 2000 microwatts/cm$^2$ at a distance of a few meters, which limits the use of this illumination process.

SUMMARY OF THE INVENTION

The present invention relates to a device making it possible, by transmitting a high power monochromatic radiation into a fibre with an excellent optical conduction and focused on the inner face of a cavity to be examined, to obtain a particularly intense photoluminescence making it possible to detect a fault or defect. An observation probe makes it possible to carry out the focusing of the monochromatic radiation and a systematic control of the inner wall of the cavity. An optical connection or junction participates in the continuity of the optical line and prevents corkscrewing of the optical fibre during the advance into the cavity of the observation probe. This apparatus comprises a monochromatic radiation source for emitting monochromatic radiation; an optical fibre connected to the radiation source by one end and to an observation probe by the other for transmitting the monochromatic radiation from the source to the probe; The observation probe has a mirror inclined with respect to the surface to be observed for directing the radiation transmitted by the optical fibre to the wall to be examined and for reflecting a return radiation to a return optical fibre for transmitting the return radiation from the observed surface towards the processing means for processing the return radiation; and a rotary optical connection placed on the fibre to permit the advance of the probe without any corkscrewing of the optical fibre.

As a result of this apparatus, it is possible excite the photoluminescence of a dye penetrant with the aid of the monochromatic radiation source, which can be constituted by a pulsed laser emitting ultraviolet radiation. The optical fibre guides the ultraviolet radiation up to the zone to be examined. Preferably the optical fibre is also used for ensuring the return of the optical signal to observation means, but two separate fibres can also be used.

Preferably the inclined mirror is mounted in rotary manner with respect to the observation probe, the latter having means for rotating said mirror.

According to one embodiment, the observation probe is constituted by a body having a connection for connecting the optical fibre to the body, a transparent tube, said rotary mirror being mounted in rotary manner within said transparent tube, optical means for focusing the radiation from the optical fibre onto the surface to be observed and means for guiding the body with respect to the cavity.

According to another embodiment, the observation probe comprises two subassemblies, namely a drive subassembly and an observation subassembly, each subassembly having a body and guidance means for guiding the body in the cavity, the drive subassembly having a motor and the observation subassembly having the rotary mirror, a flexible drive shaft connecting the motor to the rotary mirror.

The invention also relates to a rotary connection intercalated on the optical fibre to permit the said fibre to rotate without corkscrewing, said connection having a cylindrical box, a ring slidingly mounted in the box, a first base mounted in fixed manner on the box, a second base mounted in rotary manner on the sliding ring, each base having a cylindrical bore terminated by a conical part, a sphere being placed between the conical parts of the two bases and a ball bearing being placed between the box and the sliding ring.

BRIEF DESCRIPTION OF THE DRAWINGS

The invention is described in greater detail hereinafter relative to non-limitative embodiments and the attached drawings, wherein show:

FIG. 4, a second embodiment of an observation probe forming part of an endoscopic instrument according to the invention.

FIG. 5, a larger scale view compared with FIG. 4 showing an observation subassembly forming part of the endoscopy probe or tube of FIG. 4.

FIG. 5a, a perspective view of the end of the sleeve of the subassembly of FIG. 5.

FIG. 6, an illustrative diagram showing a preferred means for the translation of the mirror with respect to the surface to be observed.

FIG. 7, a rotary optical connection or link for an optical fibre forming part of an endoscopic instrument according to the invention.

DETAILED DESCRIPTION OF THE PREFERRED EMBODIMENTS

Figure 1:
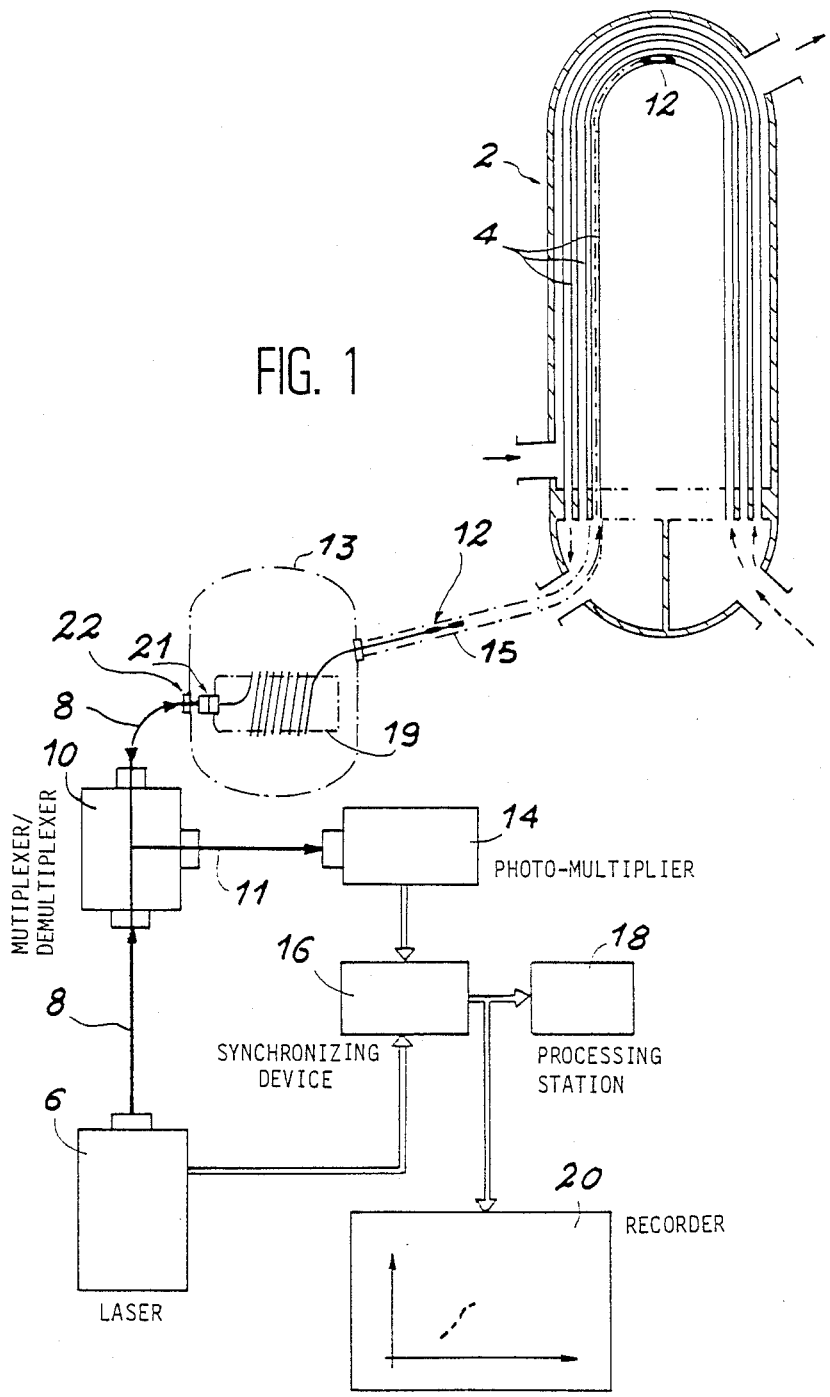
FIG. 1, a diagrammatic view of an endoscopic instrument according to the invention.

FIG. 1 is an overall diagrammatic view of an endoscopic instrument according to the invention. This instrument can e.g. be used for inspecting the U-shaped tubes of a steam generator 2. The tubes 4 of this generator, only three of which are shown so as not to overburden the drawing, have a considerable length which can exceed 100 meters and a small internal diameter of approximately 20 mm. It is therefore especially difficult to inspect the inner wall of these tubes for detecting any cracks.

However, the detection and location of faults constitute essential control operations for heat exchangers, particularly when the exchange fluids may react with one another.

The instrument according to the invention is able to satisfy this requirement. It firstly has a monochromatic radiation source 6. In the represented embodiment, said source is constituted by a pulsed nitrogen laser emitting ultraviolet light of a wavelength equal to 337.1 nanometers per 8 nanosecond pulse at a repetition rate of 50 cycles per second. Other types of pulsed or non-pulsed lasers can be used as the monochromatic radiation source, such as eximer lasers, dye lasers having frequency doublers, tunable or non-tunable lasers, etc. An appropriate penetrant liquid must obviously be chosen for each of them.

A not shown lens incorporated into laser 6 makes it possible to focus the radiation emitted by the laser onto one end of an optical fibre 8, which has an excellent conduction capacity for ultraviolet radiation and makes it possible to illuminate the penetrant liquid with a high light intensity and therefore obtain a very bright fluorescence, whose light can be returned with a limited attenuation. It is sheathed by a material having a refractive index such that the light cannot diffuse through it.

Fibre 8 is connected by its other end to a multiplexer—demultiplexer 10 whose function, as will be described hereinafter, is to separate the return light, which is visible light from the ultraviolet light emitted by the laser. At the multiplexer outlet, fibre 8 is connected to an observation probe 12, which will be described in greater detail relative to FIGS. to 2 to 6.

The light emitted by laser 6 is channelled by optical fibre 8 up to the observation probe 12, which is provided with a mirror inclined by 45° directing said radiation onto the surface to be observed. The fluorescence of the penetrant caused by said illumination is reflected towards the end of optical fibre 8 by the same mirror and is channelled back to the multiplexer—demultiplexer 10. At the multiplexer outlet or output, the visible light is directed by an optical fibre 11 (which in one embodiment is made from glass) to a photomultiplier 14, which converts the optical signal received into an electrical signal. Photomultiplier 14 is connected to a synchronization device 16 making it possible to collect the return signal from the photomultiplier in synchronism with the pulses of laser 6. The electric signal is then supplied to a processing station 18 or to a recorder 20.

Moreover, the invention also has means for e.g. pneumatically propelling the observation probe into a tube 4 to be observed. These means are of any appropriate type known from the prior art and can in particular be in accordance with French patent application No. 83 00691 of 18.1.1983. They then comprise a tight enclosure 13 which can be linked with a tube 4 to be controlled by means of a duct 15. Means, such as a not shown compressor are provided for supplying a pressurized fluid to the interior of the enclosure, as well as means such as a not shown discharge valve for discharging said fluid from the enclosure. Cable winding means constituted by a drum 19 are provided. The useful length of the optical fibre wound onto the drum is surrounded by a traction-resisting sheath and is provided with floats, i.e. olives projecting from the sheath. A rotary optical connection or link 21 placed between the fixed optical fibre and the rotary optical fibre and described relative to FIG. 7 makes it possible to unwind the cable without corkscrewing. The fixed optical fibre enters the interior of the tight enclosure through a tight passage 22.

Figure 2:
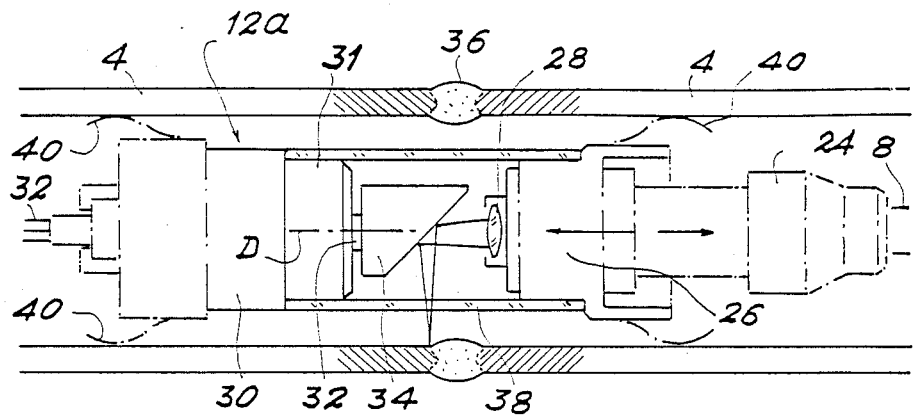
FIG. 2, a first embodiment of an observation probe forming part of an endoscopic instrument according to the invention.

FIG. 2 shows a first embodiment of an observation probe forming part of an endoscopic instrument according to the invention. Observation head 12a is connected to the end of optical fibre 8 by a connector 22 integral with said fibre. It has a base 24 and a base support 26, which receives a convergent silica lens 28. The observation head also has an electric motor 30 connected by a spindle 32 to a rotary mirror 34 inclined by 45° with respect to the longitudinal axis designated by letter D of observation probe 12a. In the represented embodiment, the laser beam is located on one edge of a weld 36, which connects two parts of a tube 4. Electric motor 30 can be supplied by any appropriate means and in particular an electric power cable 33. It is also possible to provide electric batteries integrated into the probe body.

Motor 30 is a minimotor integral with a speed reducer 31 of the same diameter and which together form an approximately 36 mm long assembly. The latter is connected to base support 36 by a high-purity silica tube 38 bonded with araldite at each of its two ends. A not shown wire impregnated with a fluorescent product is fixed to the outside of the silica tube longitudinally according to a generatrix of tube 38. This wire makes it possible to obtain a light pulse which, on recording, materializes each rotation of rotary mirror 34. Pads 40 position the probe with respect to the tube axis, so that the latter substantially coincides with the longitudinal axis D of the probe.

Figure 3:
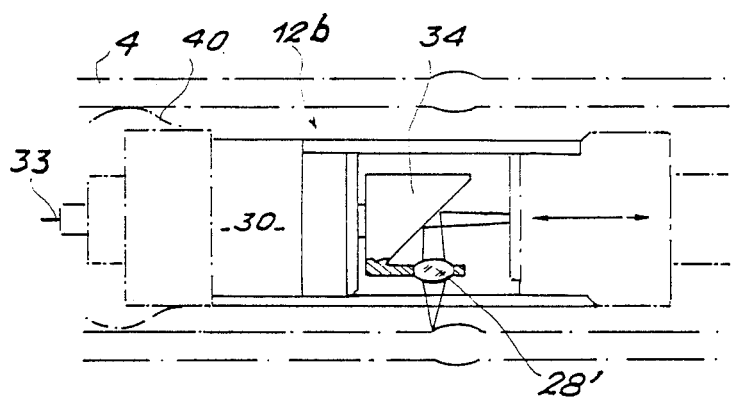
FIG. 3, a constructional variant of the observation probe of FIG. 2.

FIG. 3 shows a constructional variant of the probe 12b of FIG. 2, which differs only as a result of the differing position of the silica lens 28'. Instead of being located in the optical fibre axis, i.e. on the longitudinal axis D of the probe, said focusing lens is positioned in such a way that its axis is perpendicular to that of the inner wall of tube 4.

Probes 12a, 12b described with reference to FIGS. 2 and 3 are axially displaced by the aforementioned pneumatic device. Observation takes place during the advance, the optical system, i.e. mirror 34 permanently rotating. In the case of such a pneumatic probe drive means, the speed of movement of the probe is not perfectly regular or perfectly known. The probe movement speed and the rotation speed of rotary mirror 34 can consequently not be synchronized. Thus, the completeness of the observation of the inner surface of tube 4 can only be ensured by increasing the number of passages of probe 12a.

Thus, according to a second embodiment shown in FIGS. 4 to 6, the observation probe has means making it possible to displace the observation mirror synchronously with its rotation.

FIG. 4 shows that the probe is constituted by two subassemblies, namely a drive subassembly 12c and an observation subassembly 12d. Each subassembly has a body and guidance means 40 for guiding the body in the cavity, which is in this case constituted by the inner walls of tube 4. A flexible drive shaft 42 connects the two subassemblies. It is connected by one of its ends to an electric drive motor, which can be of the same type as used for the first embodiment, whilst its other end is connected to the spindle of the rotary mirror 34. The flexible drive shaft makes it possible for the observation probe to move within highly constricted tubes having a radius of curvature of close to 125 mm for an internal diameter of 20 mm.

FIGS. 5 and 5a show in greater detail the observation subassembly 12d of the embodiment of FIG. 4. Fibre 8 is connected by a not shown connector to the detection subassembly 12d. The light beam from fibre 8 is directed onto a silica lens 44 mounted within a ring 46 integral with the body, in such a way that the beam leaves it in parallel form. Another silica lens focuses the light beam deflected by the rotary mirror 34 onto the surface to be examined. Lens 48 is mounted within a sleeve 50, which is mobile in translation within the body 51 of observation subassembly 12d. The translation of sleeve 50 is obtained via a nut—screw system, which converts the rotary movement of the motor of the not shown drive subassembly transmitted by the flexible drive shaft 42 to the drive shaft 52 mounted on a ball bearing 54 located in the body into a translation movement. Sleeve 50 is provided with an external thread, which cooperates with an internal thread formed in element 51' of the body. Drive shaft 52 is provided at its end with a transverse pin 56, as can be seen in greater detail in FIG. 5a, which is a perspective view of the end of sleeve 50. This sleeve has a longitudinal slit 58 in which the pin 56 can slide.

Furthermore, a fixed stop 60 is provided in the element 51' of the body. Thus, sleeve 50 can move between said fixed stop 60. Another stop 49 is provided on an inner wall of sleeve 50.

FIG. 6 shows the sleeve 50 at the end of its travel opposite to that shown in FIG. 5 with lens 48' placed behind the mirror, as shown in FIG. 3. Thus, in FIG. 5, stop 49 within sleeve 50 is abutting with the fixed ring 46. However, in FIG. 6, the sleeve abuts against stop 60, which limits the travel at the other end.

When sleeve 50 abuts against one or other of the stops 60, 49, the resistance to the advance of the sleeve brought about in this way determines a sudden increase in the electric consumption of the motor of the drive subassembly. An appropriate electronic device detects this consumption increase and reverses the polarity of the motor supply current, which reverses the rotation direction of said motor and consequently the displacement direction of the sleeve. Thus, mirror 34 can perform a succession of outward and return movements within silica tube 38.

As a result of this drive system, there is a longitudinal synchronous displacement of the rotary mirror with the rotation angle thereof. During the displacement of the mirror, the observation head is fixed. Thus, this means that the pressure of the pneumatic drive device of the observation probe is interrupted. This embodiment has the advantage of making it possible to observe with a constant, known spacing a given length of tube without it being necessary to repeat the observation stage a large number of times.

FIG. 7 is a sectional view of a rotary optical connection or link making it possible to connect a fixed optical fibre section to another rotary optical fibre section. Thus, as can be seen in FIG. 1, the optical fibre penetrating the tubes of steam generator 2 is unwound from a rotary drum 19, whilst the optical fibre section connected to the multiplexer—demultiplexer 10 is fixed in rotation. It is therefore necessary to provide a rotary connection between these two optical fibre sections. The connection 21 shown in FIG. 7 makes it possible to solve this problem. This rotary connection is preferably placed on drum 19 on which is wound the optical fibre, but it can also be placed at any appropriate location for preventing twisting and corkscrewing of the fibre and its sheath during the advance of the observation probe.

This connection comprises a cylindrical box 62 formed from a flange 62a and an outer cylindrical part 62b having an internal bore. A ring 64 is received in said inner bore. It can slide therein in the longitudinal direction of the box. The longitudinal position of ring 64 is regulated by means of a plurality of screws 65. A fixed base 66 in the left-hand part of FIG. 7 passes through the flange 62a of cylindrical box 62. It is constituted by a cylindrical part and a collar. It has a longitudinal inner bore in which is received the non-rotary part of optical fibre 8 connected to multiplexer—demultiplexer 10. On it end introduced into base 66, the fibre is provided with a conventional plug permitting an appropriate centering within the base. The position of base 66 can be axially adjusted by means of screws 80 and longitudinally adjusted by means of screws 82.

A second base 68 is mounted in rotary manner within ring 64 via a bearing 70. In the same way as fixed base 66, the rotary base is formed from a cylindrical part and a collar making it possible to carry out truing or straightening of the position in a radial direction and in a longitudinal direction with respect to an intermediate ring 84 by means of screws 86, 88. One end of the rotary section of optical fibre 8 is connected to a conventional plug, introduced into the bore of rotary base 68. By means of bearing 70, base 68 can turn with respect to the first base 66. The axial play of bearing 70 is taken up by a thrust ball bearing 72. One of the rings of the latter is engaged with the intermediate ring 84, on which is mounted the inner ring of bearing 70, whilst the other ring of thrust ball bearing 72 is subject to the action of a plurality of helical springs 90 mounted in recesses of box 62 and whereof only one is shown in FIG. 7. The outer ring of bearing 70 is mounted in a bore of ring 64. As a result of the arrangement described, on tightening screws 65 ring 64, able to slide within the box, approaches the bottom of the latter, which further compresses springs 90. This force is transferred via the thrust ball bearing 72 to ring 84 and then to the inner ring of bearing 70, which makes it possible to take up the play thereof.

During the fitting of the rotary connection, the concentricity of the rotary base 68 is firstly adjusted by micrometric movements on screws 86, 88, the free end of the rotary section of optical fibre 8 being connected to a light source and a microscope is placed in front of the other end of said rotary fibre. Base 66 is then centered with the aid of micrometric movements 80, 82 and coincidence is sought between the axes of the fixed optical fibre section (right-hand part of the drawing) and the rotary fibre section (left-hand part of the drawing) by observing a maximum transmitted luminous flux. Obviously the luminous flux transmitted is at a maximum when the axes of the fibres perfectly face one another. When this maximum flux is reached, it is certain that there is concentricity of the rotary movement of the rotary fibre with respect to the fixed fibre.

The drum on which is wound fibre 8 can be mounted in the manner shown in mixed line form using bearings 92, box 62 being integral with a fixed support flange.

The apparatus according to the invention permits particularly interesting advantages, because it is then possible to detect defects and cracks of only a few microns, which cannot be detected either by direct observation using a conventional visible light endoscope, or with ultraviolet illumination such as that obtained with black light lamps. This optoelectronic method makes it possible to detect faults emerging at very considerable distances from accessible parts, particularly within small diameter, great length tubes, such as e.g. heat exchanger tubes.

The apparatus has numerous and varied applications, which are not limited to merely investigating faults and defects in metallic or non-metallic, mechanical parts of all shapes and sizes. By means of a calibration, it is also possible to establish a correspondence between the faults observed and the electronic recording obtained, so as to make it possible to draw up a library of standard fault and defect types.

What is claimed is:

1. An apparatus for remotely examining faults emerging at an inner surface of a deep cavity using photoluminescence of a substance fixed selectively in the faults of said surface, said apparatus comprising: a monochromatic radiation source; a single optical fiber having one end connected to the radiation source and another end connected to an observation probe, said single optical fiber transmitting monochromatic radiation from the source to the observation probe and also transmitting photoluminescent return radiation from the probe to a processing means; separating means placed on the optical fiber for separating said photoluminescent radiation from said monochromatic radiation; said observation probe having a mirror inclined with respect to the inner surface so as to direct the monochromatic radiation transmitted by the optical fiber to the inner surface and so as to reflect the photoluminescent return radiation to said optical fiber which conducts it to said processing means, said mirror being mounted in rotary manner with respect to the observation probe; a drive motor for rotating said mirror; a rotary optical connection placed on the optical fiber so as to permit advance of the probe without any corkscrewing of said optical fiber; means for propelling said observation probe into said deep cavity; and means for scanning said inner surface of said cavity comprising a screw element and a nut element cooperating with said screw element, one of said elements being mounted in non-rotary manner in said probe, the other of said elements being linked in rotation with the drive motor so as to displace the mirror with respect to the probe along a travel path, and means for initiating reversal of rotation direction of the motor at each end of said travel path of said mirror.

2. An apparatus according to claim 1, wherein the means for initiating reversal of the motor rotation direction at each end of the mirror travel path comprise fixed stops located at each end of the mirror travel path, and also comprise electronic means for detecting an increase in electric supply current consumption of the drive motor of the element linked with the drive motor and which automatically reverse the motor rotation direction.

3. An apparatus according to claim 1, wherein the observation probe comprises a drive subassembly and an observation subassembly, each subassembly comprising a body and guidance means for guiding said body in said cavity, the drive subassembly having a motor, the observation subassembly including said mirror and a flexible drive shaft connecting said motor to said mirror.

4. An apparatus according to claim 1, wherein the observation probe comprises a body, connection means for connecting said optical fiber to said body, a transparent tube mounted in said body, said mirror being mounted in rotary manner within the transparent tube, optical means for focusing radiation from the optical fiber onto the inner surface, and guiding means for guiding the body with respect to the cavity.

5. An apparatus according to claim 1, wherein the processing means for processing the photoluminescent radiation comprise converting means for converting said radiation reflected by the inner surface into an electric signal, and a synchronization device for collecting the electrical signal in synchronism with pulses of a laser and a recording means.

6. An apparatus according to claim 5, wherein the converting means comprises a photomultiplier.

7. An apparatus according to claim 4, wherein said guiding means comprises guide pads constituted by blades forming a spring.

8. An apparatus according to claim 1, wherein said means for propelling the observation probe into the cavity comprise a tight enclosure communicating with said deep cavity, means for introducing a pressurized fluid into said cavity and for discharging said fluid from the cavity, a cable equipped with floats, said probe being fixed to said cable, means for winding up the cable, and means for regulating introduction speed of the probe into the cavity.

9. An apparatus for remotely examining faults emerging at an inner surface of a deep cavity using photoluminescence of a substance fixed selectively in the faults of said surface, said apparatus comprising: a monochromatic radiation source; a single optical fiber having one end connected to the radiation source and another end connected to an observation probe, said single optical fiber transmitting monochromatic radiation from the source to the observation probe and also transmitting photoluminescent return radiation from the probe to a processing means; separating means placed on the optical fiber for separating said photoluminescent radiation from said monochromatic radiation; said observation probe having a mirror inclined with respect to the inner surface so as to direct the monochromatic radiation transmitted by the optical fiber to the inner surface and so as to reflect the photoluminescent return radiation to said optical fiber which conducts it to said processing means, said mirror being mounted in rotary manner with respect to the observation probe; a drive motor for rotating said mirror; a rotary optical connection placed on the optical fiber so as to permit advance of the probe without any corkscrewing of said optical fiber; and means for propelling said observation probe into said deep cavity; said rotary optical connection comprising a cylindrical box, a ring mounted in fixed manner within a bore of the box, screws for adjusting the position of said ring in a longitudinal direction within said bore of said box, a first base mounted in fixed manner on the box, screws for regulating the position of said first base with respect to the box in a longitudinal direction, screws for regulating the position of said first base with respect to said box in an axial direction, a second base which rotates within the ring by means of a bearing and an intermediate ring on which said bearing is mounted, screws for regulating the position of said second base in an axial direction and screws mounted on an intermediate ring for regulating the position of said second base in a radial direction, and a thrust ball bearing inserted between the box and the intermediate ring via compression springs so as to take up play of the bearing.

* * * * *